United States Patent
Yamazaki et al.

(10) Patent No.: US 6,778,628 B2
(45) Date of Patent: Aug. 17, 2004

(54) X-RAY COMPUTED TOMOGRAPHY APPARATUS

(75) Inventors: Masahiko Yamazaki, Shioya-gun (JP); Miwa Okumura, Kuroiso (JP); Shinsuke Tsukagoshi, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/401,680

(22) Filed: Mar. 31, 2003

(65) Prior Publication Data

US 2004/0013223 A1 Jan. 22, 2004

(30) Foreign Application Priority Data

Jul. 19, 2002 (JP) ........................................ 2002-211310

(51) Int. Cl.[7] ................................................ A61B 6/03
(52) U.S. Cl. ................................ 378/8; 378/4; 378/901
(58) Field of Search ........................... 378/4, 8, 15, 19, 378/901

(56) References Cited

U.S. PATENT DOCUMENTS 6,404,844 B1    6/2002    Horiuchi et al. ................ 378/8

FOREIGN PATENT DOCUMENTS

JP    09-245990    9/1997

*Primary Examiner*—David V Bruce
(74) *Attorney, Agent, or Firm*—Oblon, Spivak, McClelland, Maier & Neustadt, P.C.

(57) ABSTRACT

An X-ray computed tomography apparatus is provided to reconstruct image data based on projection data acquired by scanning a subject with an X-ray. A calculator is configured to calculate a dose efficiency index based on an expected dose of an X-ray radiated from an input device. The dose efficiency index indicates a diameter of a target which is identified at a predetermined detectability rate and has a predetermined CT value difference with respect to a surrounding CT value. A plan support system is configured to build up a scan planning screen on which the input expected dose is contained along with the calculated dose efficiency index. The scan planning screen is displayed on a display.

32 Claims, 15 Drawing Sheets

$\rho = f(D^N)$ $(D^N) = D \times \sqrt{\dfrac{CTDI}{CTDI^{ref}}} \times \dfrac{\rho}{\rho^{ref}} \times \sqrt{\dfrac{I}{I^{ref}}}$

FIG. 6

| No. | SCAN MODE | EXPO. CONT. | CTDI (mGy) | DLP (mGY/cm) | mAs | DEI (D(mm) at 50%) | D (mm) at XX% | DETECTABILITY RATE (%) at XXmm | DEI at XX(ρ) |
|---|---|---|---|---|---|---|---|---|---|
| 1 | HELICAL | ON | 20 | 100 | 150 | 15.0 (±0.5) | | | |
| | | | | | | | | | |
| | | | | | | | | | |
| | | | | | | | | | |
| | | | | | | | | | |

MAIN INFO. | RECONSTRUCTION INFO. | WINDOW INFO. | DOSE INFO.

CT VALUE DIFFERENCE

DEI CONSTANT CONTROL

SAMPLE IMAGE (PHANTOM)

SCANOGRAM

DETECTABILITY PROFILE

COPY | DELETE | RETURN | CTDI UPDATE | PROFILE DISPLAYING | CONFIRM

FIG. 11

| No. | SCAN MODE | EXPO. CONT. | CTDI (mGy) | DLP (mGy/cm) | mAs | DEI (D (mm) at 50%) | D (mm) at XX% | ▼ | DETECTABILITY RATE (%) at XXmm | ▼ | DEI at XX(ρ) | ▼ |
|---|---|---|---|---|---|---|---|---|---|---|---|---|
| 1 | HELICAL | ON | 20 | 100 | 150 | 15.0±0.5 | 19.0±3 | 80 | 18.5±1.5 | 10 | | |
| | | | | | | | | | | | | |
| | | | | | | | | | | | | |
| | | | | | | | | | | | | |
| | | | | | | | | | | | | |

MAIN INFO. | RECONSTRUCTION INFO. | WINDOW INFO. | DOSE INFO.

CT VALUE DIFFERENCE | DEI CONSTANT CONTROL

SAMPLE IMAGE (PHANTOM) | SCANOGRAM | DETECTABILITY PROFILE

COPY | DELETE | RETURN | CTDI UPDATE | PROFILE DISPLAYING | CONFIRM

FIG. 13

| No. | SCAN MODE | EXPO. CONT. | CTDI (mGy) | DLP (mGy/cm) | mAs | DEI (D (mm) at 50%) | D (mm) at XX% | DETECTABILITY RATE (%) at XXmm | DEI at XX (ρ) |
|-----|-----------|-------------|------------|--------------|-----|---------------------|---------------|-------------------------------|---------------|
| 1 | HELICAL | ON | 20 | 100 | 150 | 15.0±0.5 | 19.0±3 | 18.5±1.5 | 19.0±2.5 |
|   |         |    |    |     |     |          | ▼ 80     | ▼ 10       | ▼ 0.7    |

SAMPLE IMAGE (PHANTOM)

SCANOGRAM

DETECTABILITY PROFILE

MAIN INFO. | RECONSTRUCTION INFO. | WINDOW INFO. | DOSE INFO.
CT VALUE DIFFERENCE | DEI CONSTANT CONTROL

COPY | DELETE | RETURN | CTDI UPDATE | PROFILE DISPLAYING | CONFIRM

FIG. 17

X-RAY COMPUTED TOMOGRAPHY APPARATUS

CROSS-REFERENCE TO RELATED APPLICATIONS

This application is based upon and claims the benefit of priority from the prior Japanese Patent Application No. 2002-211310, filed Jul. 19, 2002, the entire contents of which are incorporated herein by reference.

BACKGROUND OF THE INVENTION

1. Field of the Invention

The present invention relates to an X-ray computed tomography apparatus.

2. Description of the Related Art

An X-ray computed tomography apparatus is intended to provide profile information of an inside of a subject based on an intensity of an X-ray which has passed through the subject, having an important role in a number of practices of medicine including disease diagnosis, treatment, operation planning, etc. At the stage of scanning planning, a tube current-time lapse product (mAs) is determined. A number of conventional X-ray computed tomography apparatus display on a scan planning screen thereof CT Dose Index (CTDI), which indicates a radiation dose defined by the U.S. Food and Drug Administration (USFDA). An operator of the X-ray computed tomography apparatus determines an "mAs" value with reference to "CTDI". A specific X-ray computed tomography apparatus displays on its scan planning screen a "CTDI" value as well as an image quality evaluation index called an image standard deviation (image SD). The operator determines an "mAs" value with reference to "CTDI" and "image SD".

The operator, however, cannot know a so-called low-contrast resolution, which determines a relationship between a certain density of an object and its minimum size that can be identified. The operator, therefore, is required to have skills in order to determine the "mAs" value appropriately.

BRIEF SUMMARY OF THE INVENTION

It is an object of the invention to provide an X-ray computed tomography apparatus which enables easy setting of appropriate scanning conditions.

An X-ray computed tomography apparatus according to a first aspect of the invention for reconstructing image data based on projection data acquired by scanning a subject with an X-ray, comprising:

an input device configured to input an expected dose of the X-ray;

a calculator configured to calculate a Dose Efficiency index (DEI) based on the expected dose, the DEI indicating a diameter of a target identified at a predetermined detectability rate and the target having a predetermined CT value difference with respect to a surrounding CT value;

a plan support system configured to build up a scan planning screen on which the input expected dose is contained along with the calculated DEI; and a display configured to display the scan planning screen.

An X-ray computed tomography apparatus according to a second aspect of the invention for reconstructing image data based on data acquired by scanning a subject with an X-ray, comprising:

an input device configured to input a DEI, the DEI indicating a diameter of a target identified at a predetermined detectability rate and the target having a predetermined CT value difference with respect to a surrounding CT value;

a calculator configured to calculate an expected dose of the X-ray based on the DEI;

a plan support system configured to build up a scan planning screen on which the input DEI is contained along with the calculated expected dose; and a display configured to display the scan planning screen.

An X-ray computed tomography apparatus according to a third aspect of the invention for reconstructing image data based on data acquired by scanning a subject with an X-ray, comprising:

an input device configured to input an arbitrary detectability rate and a diameter of a target identified with the detectability rate;

a calculator configured to calculate an expected dose of the X-ray based on the input detectability rate and the input target diameter;

a plan support system configured to build up a scan planning screen on which the input detectability rate and the input target diameter are contained along with the calculated expected dose; and a display configured to display the scan planning screen.

An X-ray computed tomography apparatus according to a fourth aspect of the invention for reconstructing image data based on data acquired by scanning a subject with an X-ray, comprising:

an input device configured to input an expected dose of the X-ray and an arbitrary DEI, the DEI indicating a diameter of a target identified at a predetermined detectability rate;

a calculator configured to calculate a CT value difference with respect to a surrounding CT value of the target so that the input DEI may be realized by the input expected dose of the X-ray;

a plan support system configured to build up a scan planning screen on which the input expected dose of the X-ray and the input DEI are contained along with the calculated CT value or a value derived therefrom; and a display configured to display the scan planning screen.

An X-ray computed tomography apparatus according to a fifth aspect of the invention for reconstructing image data based on projection data acquired by helically scanning a subject with an X-ray sent from an X-ray tube, comprising:

an input device configured to input a DEI, the DEI indicating a diameter of a target identified at a predetermined detectability rate and the target having a predetermined CT value difference with respect to a surrounding CT value;

a calculator configured to calculate an expected dose of the X-ray which corresponds to each of a plurality of positions so that the input DEI may be maintained at the plurality of positions; and a controller configured to dynamically alter a tube current of the X-ray tube in accordance with the expected dose of the X-ray calculated at the plurality of positions.

An X-ray computed tomography apparatus according to a sixth aspect of the invention for reconstructing image data based on projection data acquired by scanning a subject with an X-ray, comprising:

a calculator configured to calculate a DEI based on a does of the X-ray, the DEI indicating a diameter of a target identified at a predetermined detectability rate and the target having a predetermined CT value difference with respect to a surrounding CT value; and a stored data file generator configured to generate a storage data file, the storage data file containing therein the image data along with data relating to the calculated DEI.

An X-ray computed tomography apparatus according to a seventh aspect of the invention for reconstructing image data based on projection data acquired by scanning a subject with an X-ray, comprising:

a calculator configured to calculate a DEI based on a does of the X-ray, the DEI indicating a diameter of a target identified at a predetermined detectability rate and the target having a predetermined CT value difference with respect to a surrounding CT value; and a print data generator configured to generate print data from the image data and the calculated DEI.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

An X-ray computed tomography apparatus according to a eighth aspect of the invention for reconstructing image data based on data acquired by scanning a subject with an X-ray, comprising:

an calculator configured to calculate a parameter relative to the image data; and a display configured to display an error range of the parameter to be calculated.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 6 is an illustration for showing an X-ray conditions setting screen built up by a plan support system of FIG. 1;

FIG. 11 is an illustration for showing an X-ray conditions setting screen built up by the plan support system of FIG. 1;

FIG. 13 is an illustration for showing another X-ray conditions setting screen built up by the plan support system of FIG. 1;

FIG. 17 is an illustration for showing X-ray conditions setting screen built up by the plan support system of FIG. 1, especially showing a CT value difference window which is popped up when a "CT value difference" button is clicked;

DETAILED DESCRIPTION OF THE INVENTION

The following will describe preferred embodiments of the invention with reference to drawings. It is to be noted that the invention is applicable to both an X-ray computed tomography apparatus which reconstructs image data based on data (projection data) acquired by scanning a subject with an X-ray and an X-ray diagnostic apparatus which generates a transmission plane image data acquired by imaging a subject with an X-ray. The following describes the invention with reference to an X-ray computed tomography apparatus.

The X-ray computed tomography apparatus may come in a variety of types such as a ROTATE/ROTATE type in which an X-ray tube and a radiation detector rotate integrally around a subject, a STATIONARY/ROTATE type in which only an X-ray tube rotates around a subject, etc., to any of which the invention can be applied. The following will describe the ROTATE/ROTATE type, which is mainly used recently. Furthermore, to reconstruct one slice of tomogram data, it is necessary to acquire projection data of one round of a subject, that is, projection data of about 360° or that of 180° plus a view angle even by a half-scan system. In either case of the system, the invention is applicable. The following will describe the invention with reference to the half-scan system. Furthermore, as a mechanism which converts an incident X-ray into electric charge are there mainly used an indirect conversion system which converts an X-ray into light by a phosphor such as a scintillator and then into electric charge by a photo-electric transfer element such as a photo-diode and a direct conversion system which utilizes the photo-conduction phenomenon, that is, generation of an electron-and-hole pair in a semiconductor by an X-ray and movement thereof to an electrode. Although the X-ray detector may be of either system, the following will describe it as to be of the former indirect type of system. Furthermore, recently, there has been commercialized a so-called multi-tube-bulb type X-ray computed tomography apparatus in which a rotary ring is mounted with a plurality of pairs of an X-ray tube and an X-ray detector, accompanied by developments of its peripheral technologies. The invention can be applied to both a conventional single-tube-bulb type X-ray computed tomography apparatus and a multi-tube-bulb type X-ray computed tomography apparatus. The following will describe the single-tube-bulb type one. Furthermore, a detector has been mounted in multiple rows; in fact, recently, 40 rows (40 segments) or more of detectors are practically mounted in an apparatus. The invention can be applied to, of course, an X-ray computed tomography apparatus equipped with a conventional single-slice type detector and also to the one equipped with a multi-slice type detector. The following will describe the invention with reference to an X-ray computed tomography apparatus equipped with a multi-slice type detector.

Figure 1:
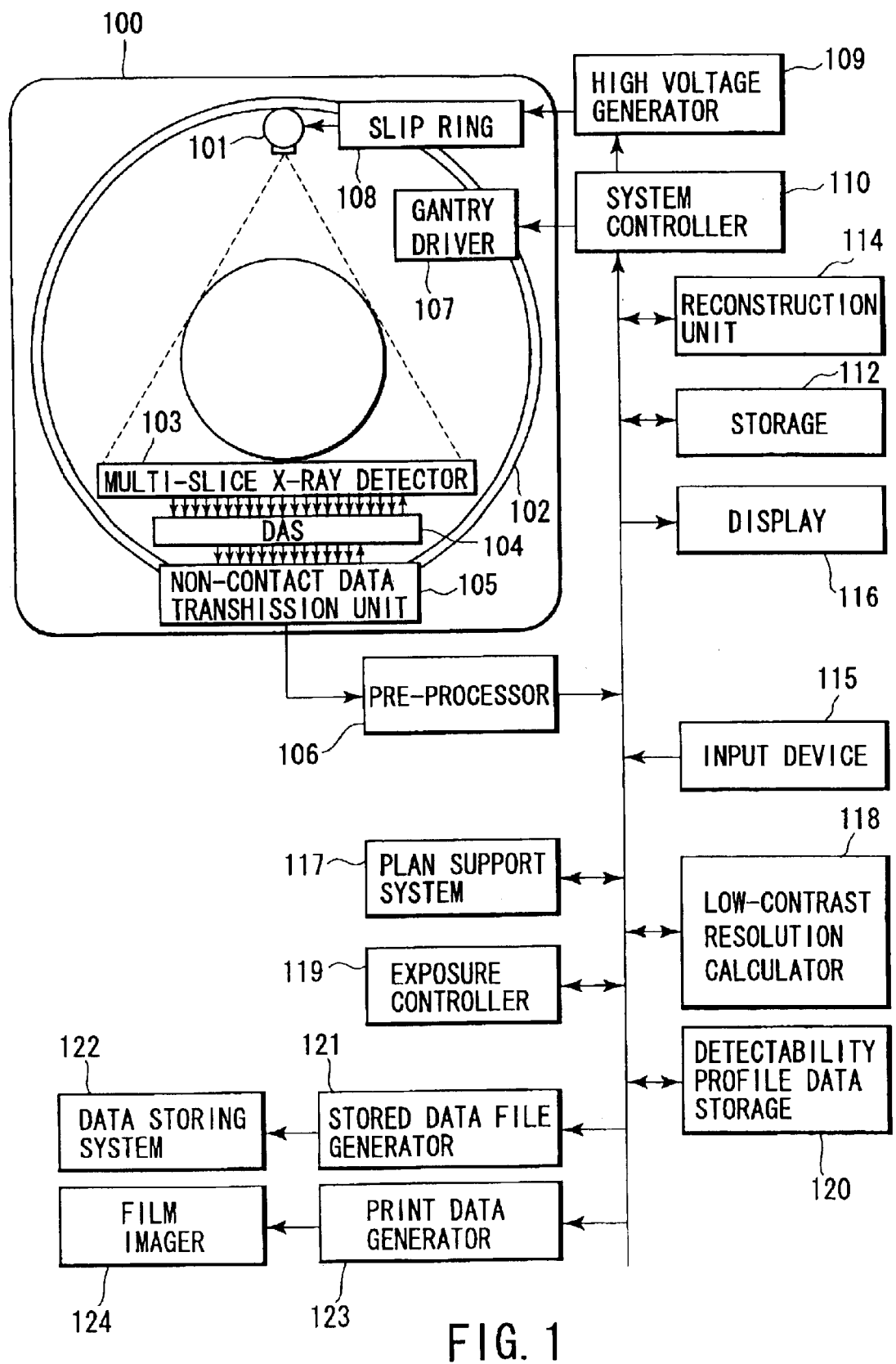
FIG. 1 is a block diagram for showing a configuration of an embodiment of a X-ray computed tomography apparatus of the invention.

FIG. 1 shows a configuration of an X-ray computed tomography apparatus related to the embodiment. A gantry 100 has an X-ray tube 101 and a multi-slice X-ray detector 103. The X-ray tube 101 and the multi-slice X-ray detector 103 are mounted to a ring-shaped rotary frame 102 which is supported in a rotary manner. The multi-slice X-ray detector 103 is opposed in arrangement to the X-ray tube 101. When the rotary frame 102 is being rotated as driven by a gantry driver 107, a tube voltage is applied continuously or intermittently on the X-ray tube 101 from a high voltage generator 109 through a slip ring 108. This causes the X-ray tube 101 to radiate an X-ray continuously or intermittently. The multi-slice X-ray detector 103 has a plurality of modules in each of which detection elements which detect an X-ray having passed through a subject are arrayed in an (m by n) matrix. The plurality of modules are arrayed with respect to a channel direction. It is thus possible to make up a large scale configuration which has detectors as many as, for example, 40 rows times 916 channels.

A data acquisition circuit 104, which is generally referred to as Data Acquisition System (DAS), converts a signal output for each channel from the detector 103 into a voltage signal, amplifies it, and converts it into a digital signal. This data (raw data) is sent via a non-contact data transmission unit 105 to a pre-processor 106 outside the gantry, where it undergoes correction processing such as sensitivity correction and is stored in a storage 112 as so-called projection data, which is just about to undergo reconstruction processing.

The storage 112 is connected to a reconstruction unit 114, a display 116, an input device 115, a plan support system 117, a low-contrast resolution calculator 118, an exposure controller 119, a detectability profile data storage 120, a stored data file generator 121, a data storing system 122, a print data generator 123, and a film image 124 and also, via a data/control bus 120, to a system controller 110.

Technical knowledge is required to optimize scan conditions such as a tube voltage, a tube current, an X-ray radiation time lapse, etc. as well as reconstruction conditions such as a slice thickness, the number of slices, a matrix size, etc. The plan support system 117 has been developed to use this technical knowledge as a basis in order to permit even an experienced person with little technical knowledge to set almost the same conditions as above. The plan support system 117 has this conditions optimization function as well as a function to build up a scan planning screen having a Graphical User Interface (GUI).

The low-contrast resolution calculator 118 is provided to calculate a variety of indexes relating to a DEI as a low-contrast resolution. The DEI is expressed as a diameter of a target indicating a detectability rate (identification rate) of 50% in an image which is reconstructed from projection data acquired by scanning, with an X-ray having a certain dose, targets having a certain density difference (CT value difference) with respect to the surroundings. That is, the DEI is an index that indicates how small targets can be identified in an image at a probability of 50%.

The dose in this case is given as a CTDI (CT dose index), which is a typical index. The CTDI is acquired as a value of a quotient of a division of an integration of a radiation profile along a vertical line on a slice plane by a product of a slice thickness and the number of slices. As well known, a tube current-time lapse product can be derived from a CTDI value.

The low-contrast resolution calculator 118 calculates an expected dose of an X-ray required to achieve a specified DEI value, that is, "mAs" in this case. The exposure controller 119 controls a tube current of the X-ray tube 101 in accordance with a calculated mAs value. The exposure controller 119 dynamically alters a tube current of the X-ray tube in accordance with the movement of a top plate based on mAs values calculated at a plurality of positions in the case of, for example, helical scanning.

The detectability profile data storage 120 holds data relating a plurality of detectability rate profiles in each of which an mAs value and a phantom diameter are different from each other. A detectability rate profile represents a function of a detectability rate with respect to a target diameter. A phantom diameter corresponds to a transmission dose essentially.

The stored data file generator 121 generates a storage data file which contains image data and DEI data which is given when projection data which provides a basis of this image data is acquired. Typically, a storage data file is comprised of a header region and a data region. Image data is written into the data region. DEI data is written into the header region along with patient information etc. A storage data file is stored on a mass storage medium such as an optical disc etc. of the data storing system 122. The print data generator 123 generates frame data for printing from image data and DEI data which is given when projection data which provides a basis of this image data is acquired. A printer, for example, the film imager 124 prints an image and attendant information such as a DEI on a film in accordance with the print data.

Figure 2:
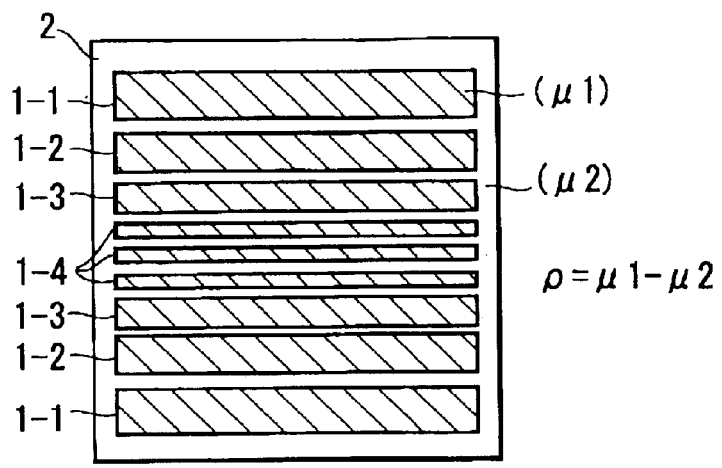
FIG. 2 is a vertical cross-sectional view for showing a phantom according to the embodiment.

Next, a DEI is described below. FIG. 2 shows a vertical cross-sectional view of a column-shaped phantom. The phantom is comprised of a base 2 which has an absorption coefficient of $\mu 2$ and a plurality of column-shaped targets 1-1, 1-2, 1-3, and 1-4 which are buried into the base 2 and have an absorption coefficient of $\mu 1$. The target 1-1 has a diameter of, for example, 15 mm. The targets 1-2, 1-3, and 1-4 have diameters of 12 mm, 9 mm, and 6 mm, respectively. A density difference is given as a difference in absorption coefficient of the target 1 with respect to the base 2. The density difference appears as a difference in CT value (CT value difference) of the target 1 with respect to a CT value of the base 2.

Figure 3:
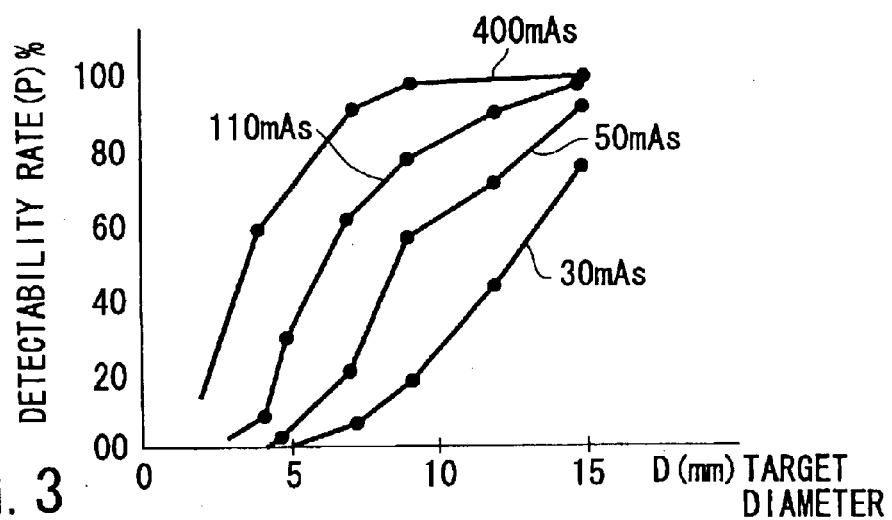
FIG. 3 is a graph for showing a distribution of a detectability rate with respect to a target diameter according to the embodiment.

In a condition where a tube voltage and a slice thickness are constant, this phantom is imaged five times as altering a tube current-time lapse product mAs. A plurality of images thus acquired are used as an object, to permit a plurality of evaluators to repeatedly evaluate a limit diameter of the target 1 that can be identified visually. FIG. 3 shows a relationship between a target diameter and a detectability rate (rate of the number of times of visually identifying the target with respect to the number of trials made by all of the evaluators) for each tube current-time lapse product (mAs). It is to be noted that preferably the evaluator is a person in charge of reading out the images or a doctor who is employed in a hospital in which the relevant apparatus is installed.

Figure 4:
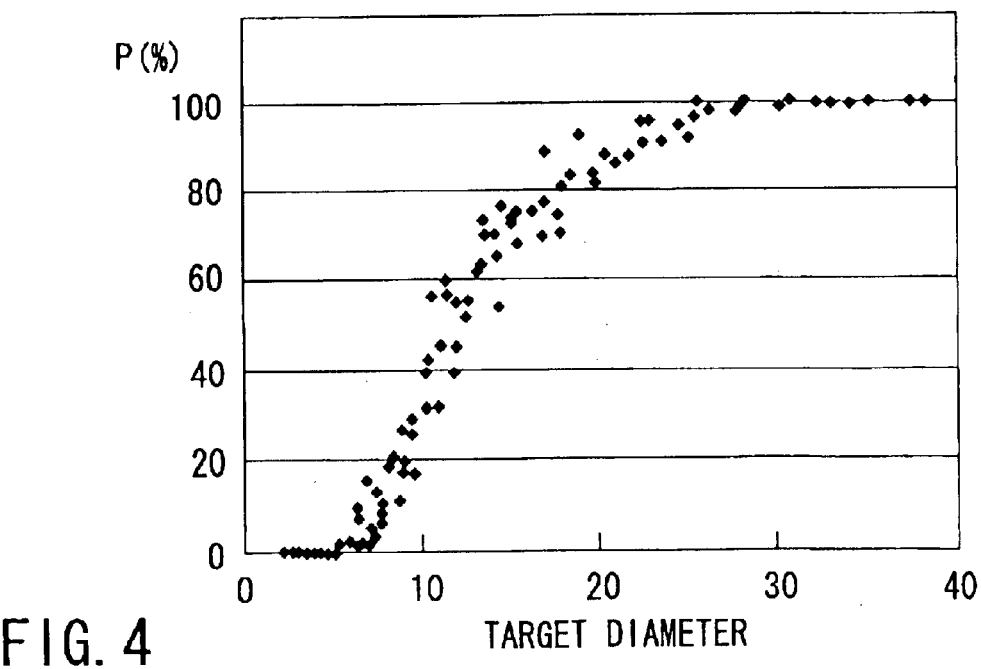
FIG. 4 is a graph for showing a distribution of FIG. 3 normalized with "CTDI" according to the embodiment.
Figure 5:
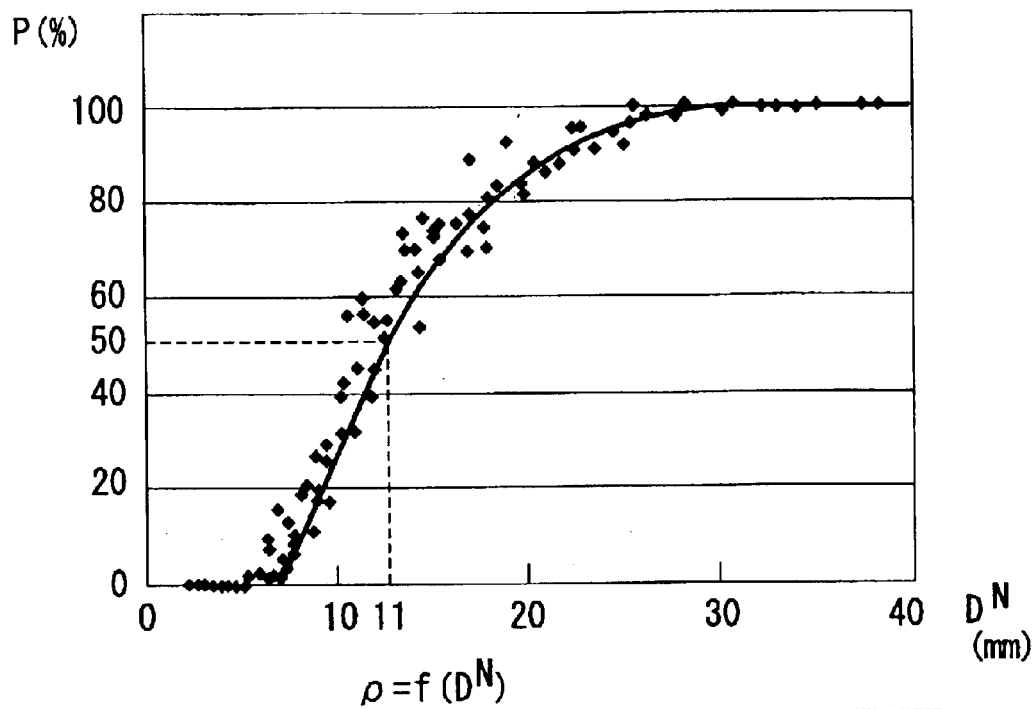
FIG. 5 is a graph for showing an approximate curve of the distribution of FIG. 4 according to the embodiment.

FIG. 4 shows a distribution normalized with "CTDI". FIG. 5 shows an approximate curve (detectability rate profile) of the distribution normalized with a CTDI. This detectability rate profile has its CTDI dependency eliminated. A normalized relationship between a target diameter and a detectability rate represents performance related to a spatial resolution inherent to the apparatus.

A DEI is defined as a diameter of a target that can be recognized at a detectability rate (probability) of 50%. In an example of FIG. 5, the DEI is 11 mm. Targets having a diameter of 11 mm can be detected at a probability of 50%.

A detectability rate p depends on a target diameter D, a CTDI, a density difference ρ, and a transmission dose I. That is, it is expressed as follows with f as supposed to be a detectability rate profile function (approximate curve function):

$$P=f(D, CTDI, \rho, I) \quad (1)$$

By normalizing a target diameter D with a reference dose $CTDI^{ref}$, a reference density difference $\rho^{ref}$, and a reference transmission dose $I^{ref}$, a simplified relationship between a detectability rate p and a normalized target diameter $D^N$ can be derived as follows:

$$P=f(D^N) \quad (2)$$

$$D^N=D\times(CTDI/CTDI^{ref})^{1/2}\times(\rho/\rho^{ref})\times f\{(I/I^{ref})^{1/2}\} \quad (3)$$

Thus, a relationship between the normalized target diameter $D^N$ and the detectability rate p can be acquired.

The low-contrast resolution calculator 118 can set any given four parameters of the CTDI, the density difference ρ, the transmission dose I, the detectability rate p, and the target diameter D by using the above equations, to thereby calculate the remaining fifth parameter. For example, based on a set value of CTDI, a target diameter having a detectability rate p of 50%, that is, DEI can be calculated. Normally, the density difference ρ and the transmission dose I are given as a reference value.

A DEI value thus calculated as well as its error range are displayed in a representation of "DEL (D(mm) at 50%)" along with typical dose information as "CTDI", "DLP", "mAs" in a tab window of "dose information (DOSE INFO.)" on a scan planning screen shown in FIG. 6 made up by the expert system 117.

The error range is indicated as ±0.5 mm in the example shown in FIG. 6. This error range is determined on the basis of a divergence of a plurality of target diameters corresponding to each of detectability rates in a distribution of FIG. 5. An error range corresponding to each detectability rate is stored as correlated to a detectability rate profile in the detectability profile data storage 120.

Figure 7:
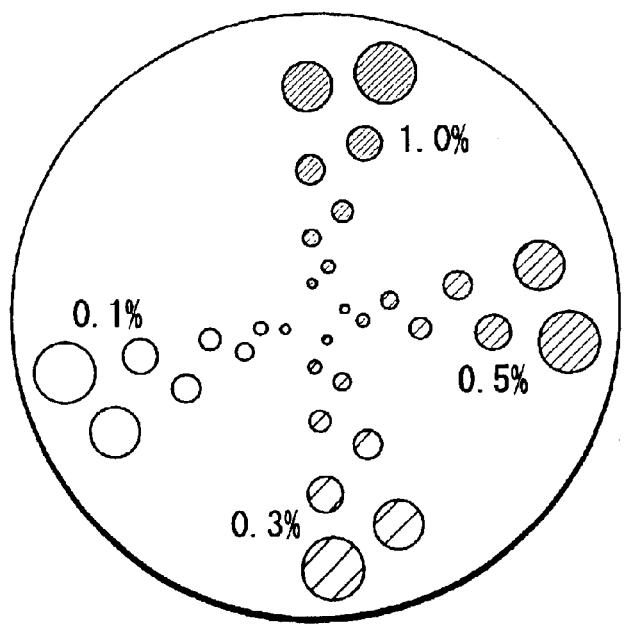
FIG. 7 is an illustration for showing a sample image which corresponds to a DEI and which is displayed on the screen of FIG. 6.

In the left top field of the scan planning screen is there displayed a sample image of the phantom corresponding to the DEI as shown in FIG. 7. A plurality of sample images which correspond to a plurality of DEI values are stored in the detectability profile data storage 120 beforehand. A sample image that corresponds to a calculated DEI value is read out selectively from the detectability profile data storage 120 into the plan support system 117.

Figure 8:
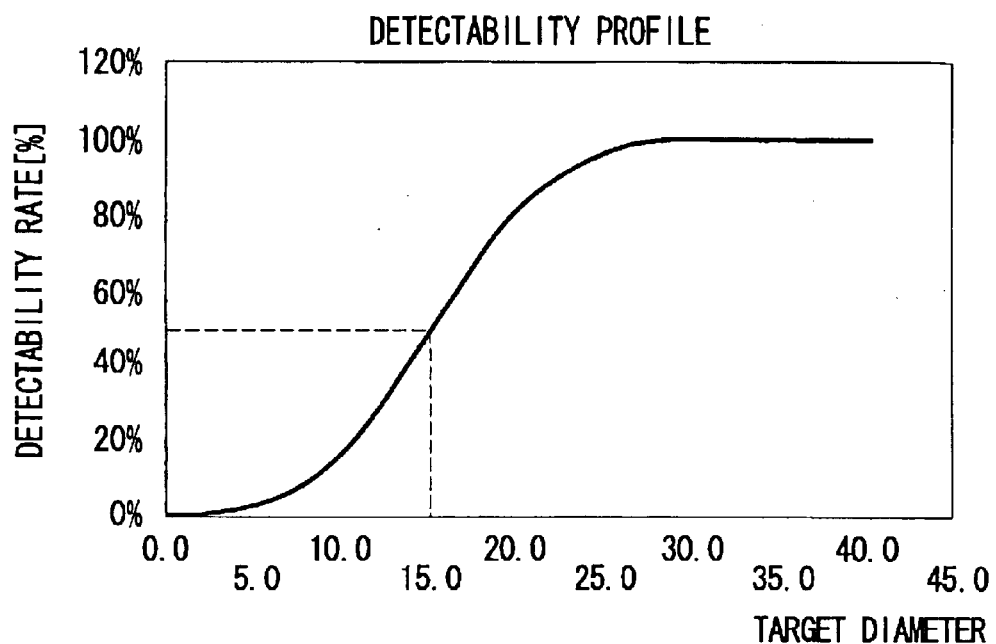
FIG. 8 is a graph for showing a detectability rate displayed on the screen of FIG. 6.

In the right top field of the scan planning screen is there displayed a detection rate profile corresponding to a set value of CTDI along with a line (broken line indicating the DEI) as shown in FIG. 8.

In the window are displayed along with the DEI the following:

"target diameter corresponding to desired detectability rate p specified by operator";

"detectability rate p corresponding to desired target diameter specified by operator": and "DEI corresponding to desired CT value difference specified by operator".

Those items of "target diameter corresponding to arbitrary detectability rate p", "detectability rate p corresponding to arbitrary target diameter", and "DEI corresponding to arbitrary CT value difference" are calculated along with the DEI value by the low-contrast resolution calculator 118.

Figure 10:
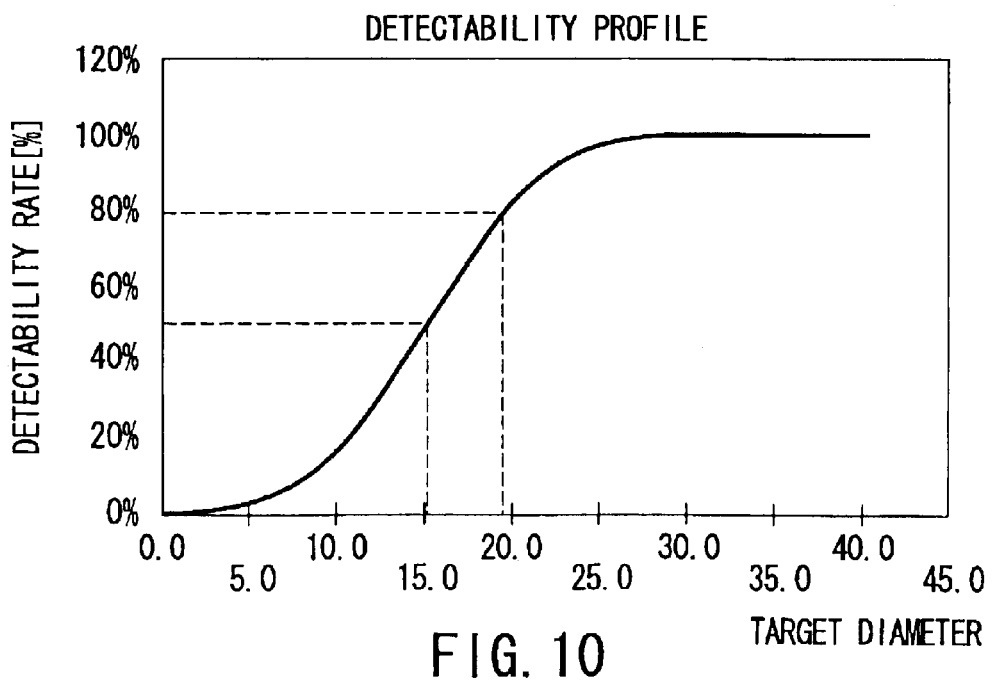
FIG. 10 is a graph for showing a detectability rate profile synthesized on the screen of FIG. 9.
Figure 9:
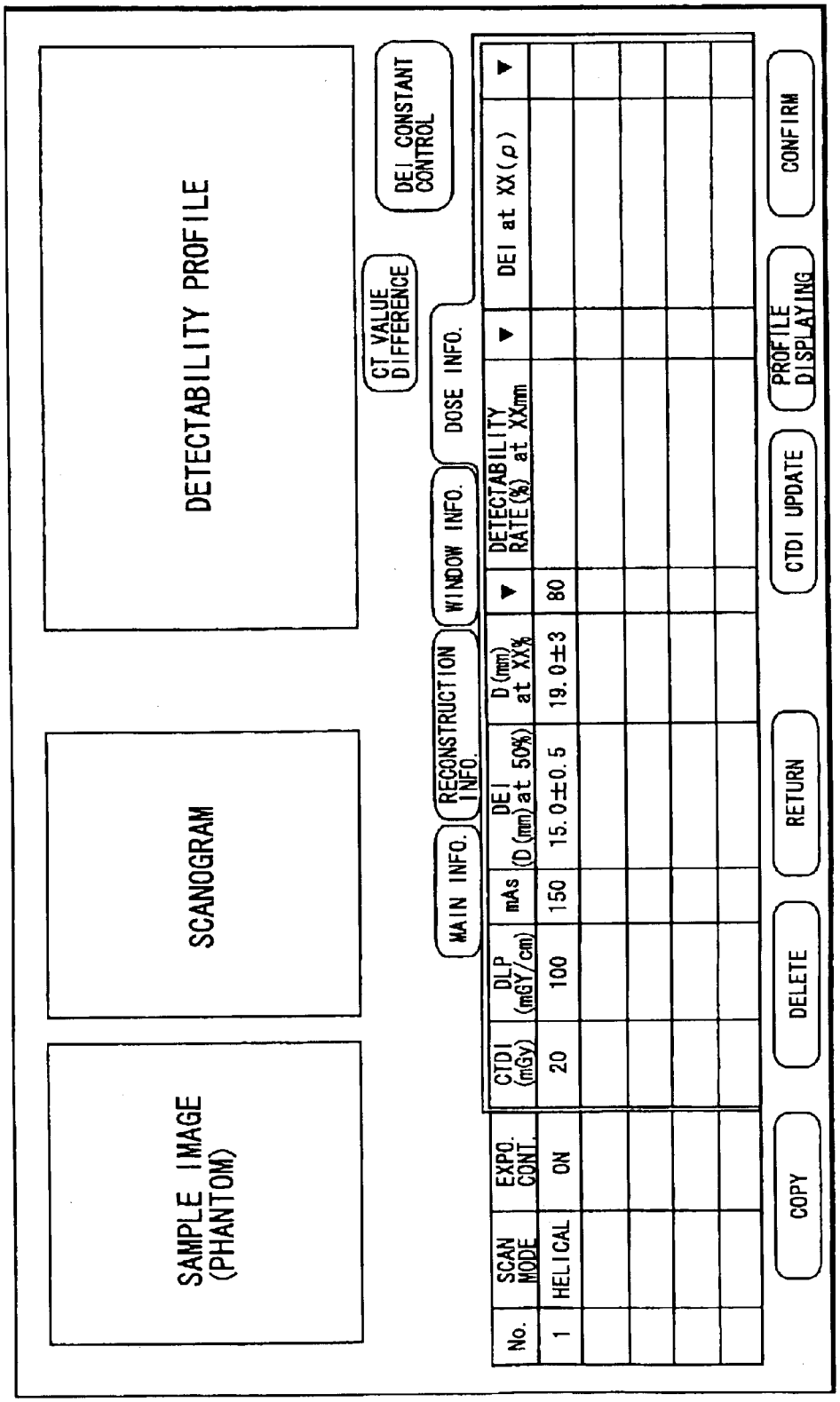
FIG. 9 is an illustration for showing another X-ray conditions setting screen built up by the plan support system of FIG. 1.

For example, as shown in FIG. 9, a "target diameter corresponding to desired detectability rate p specified by operator" is displayed along with an error range in a representation of "D(mm) at XX%". An arbitrary detectability rate p can be entered as a numeral or selected from a pull-down menu on the left side of this representation. An example of FIG. 9 displays a target diameter exhibiting a detectability rate of 80% is 19.0 mm and its error range is ±3 mm. FIG. 10 shows a detectability rate profile displayed in the right top field of this scan planning screen. In the graph are there displayed along with a line (broken line) indicating a DEI this entered detectability rate of 80% and the corresponding target diameter of 11 mm as indicated by a line (broken line).

Figure 12:
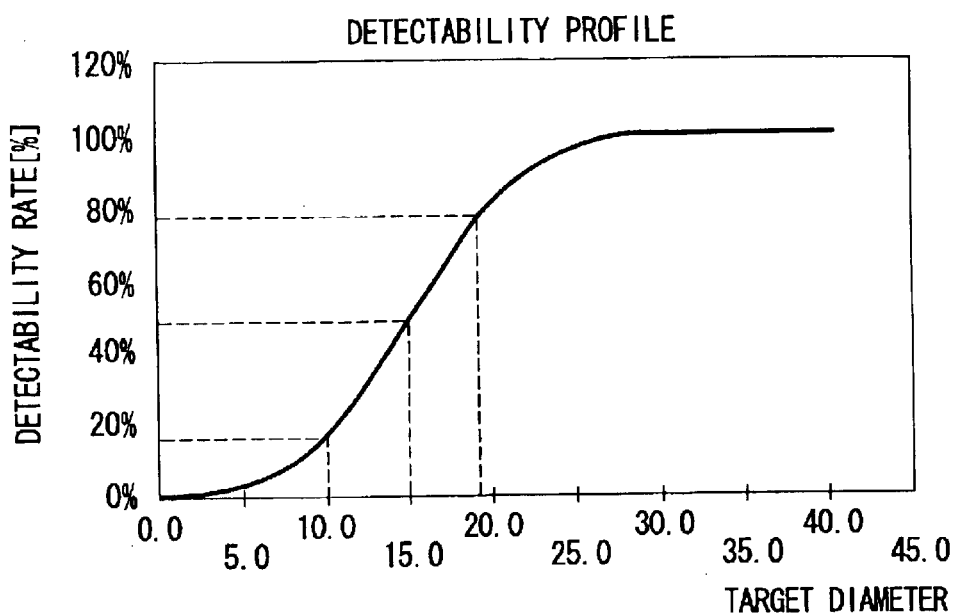
FIG. 12 is a graph for showing a detectability rate profile displayed on the screen of FIG. 11.

Furthermore, as shown in FIG. 11, a "detectability rate p corresponding to desired target diameter specified by operator" is displayed along with its error range in a representation of "DETECTABILITY RATE (%) at XXmm". An arbitrary target diameter can be entered as a numeral or selected from the pull-down menu on the right side of this representation. An example of FIG. 11 displays that a target having a diameter of 10 mm exhibits a detectability rate (recognition rate) of 18.5%. FIG. 12 shows a detectability rate profile displayed in the right top field of the scan planning screen. In the graph are there displayed a line indicating a 10-mm target diameter and a corresponding detectability rate of 18.5% along with a line (broken line) indicating a DEI and a line (broken line) indicating this entered detectability rate of 80% and the corresponding target diameter of 11 mm.

Figure 14:
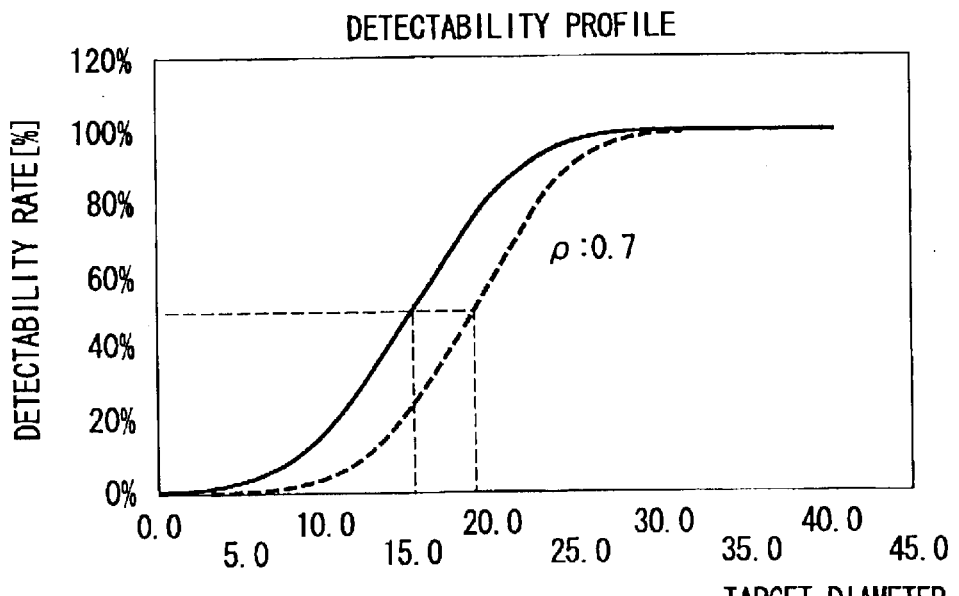
FIG. 14 is a graph for showing a detectability rate profile displayed on the screen of FIG. 13.

Furthermore, as shown in FIG. 13, a "DEI (target diameter having detectability rate of 50%) corresponding to desired density difference specified by operator" is displayed along with its error range in a representation of "DEI at XX(ρ)". An arbitrary density difference can be entered as a numeral or selected from the pull-down menu on the left side of this representation. An example of FIG. 13 displays that a DEI in a case where the density difference is 0.7 is 19.0 mm and its error range is ±2.5 mm. FIG. 14 shows a detectability rate profile displayed in the right top field of the scan planning screen. In this graph are there displayed along with (density difference is equivalent to a reference density difference) a detectability rate profile in the case where the density difference is 0.7 and its DEI.

Figure 17:
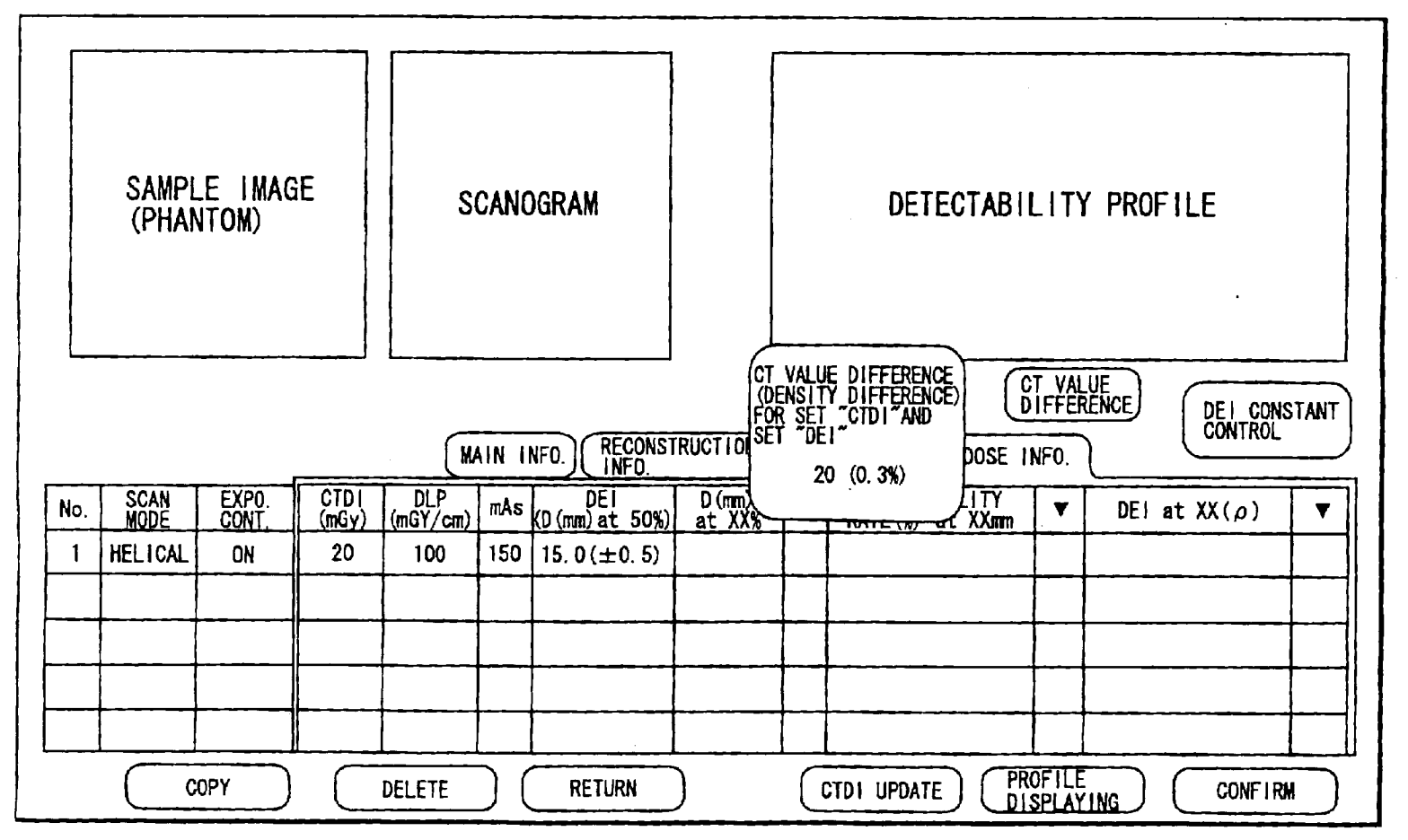

Furthermore, by clicking the CT VALUE DIFFERENCE CALCULATE button, the calculator 118 calculates a CT value difference (density difference) required to realize a DEI value set by the operator, based on a CTDI value set by the operator. As shown in FIG. 17, the expert system 117 displays a calculated CT value difference (density difference) on the scan planning screen. Based on the displayed CT value difference (density difference), a technician in charge of imaging can know to some extent a quantity of a barium mean to be injected into the subject.

A detectability rate profile can be utilized in dose control (exposure control) during conventional scanning (stepping scanning) in which helical scanning or single-or multi-slice scanning is repeated as involving stopping and moving of the top plate. This function is referred to as DEI constant control. The DEI constant control function can be set by clicking the "DEI CONSTANT CONTROL" button on the scan planning screen.

Figure 15:
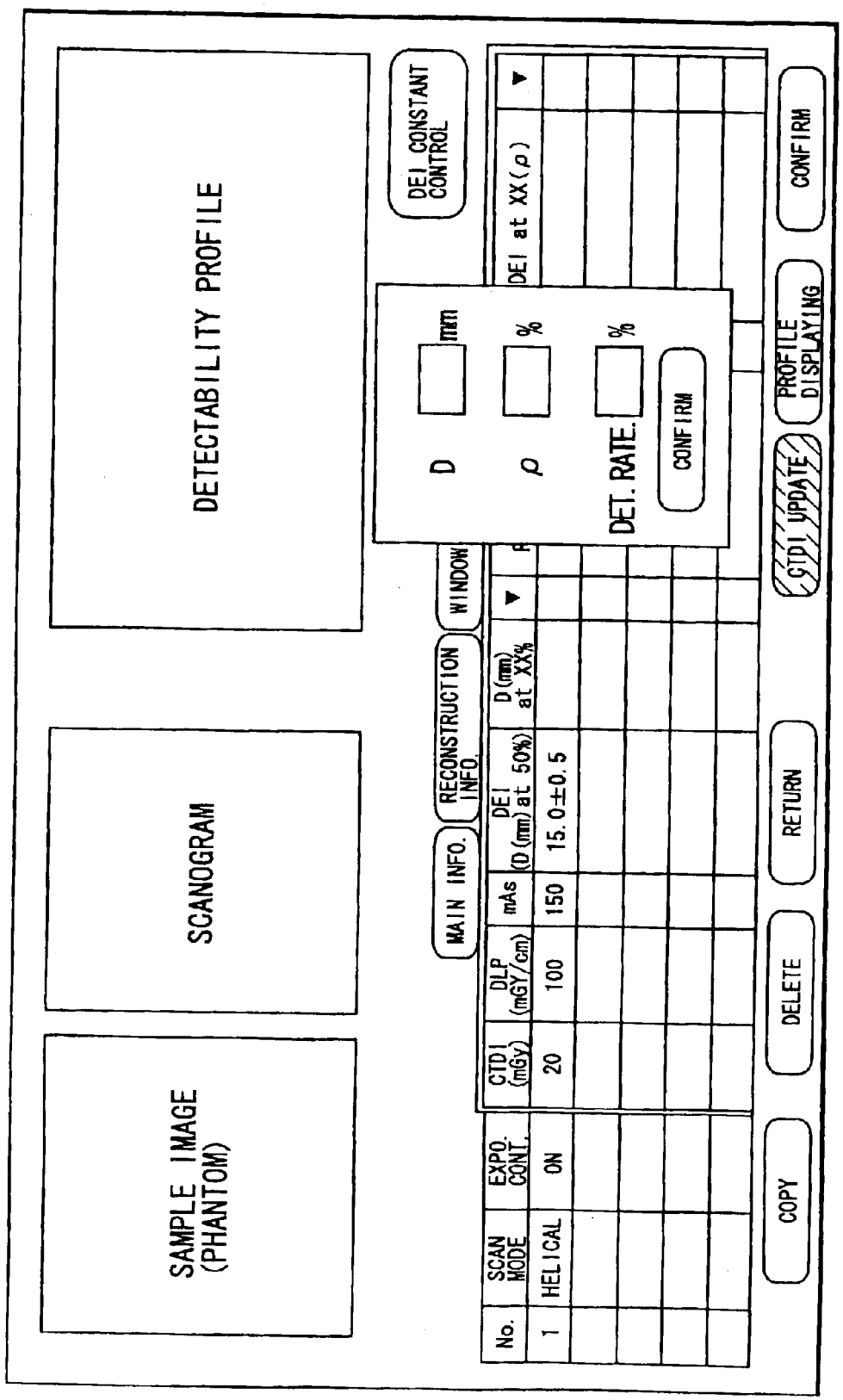
FIG. 15 is an illustration for showing another X-ray conditions setting screen built up by the plan support system of FIG. 1, especially showing an update conditions setting window which is popped up when a "CTDI" button is clicked.
Figure 16:
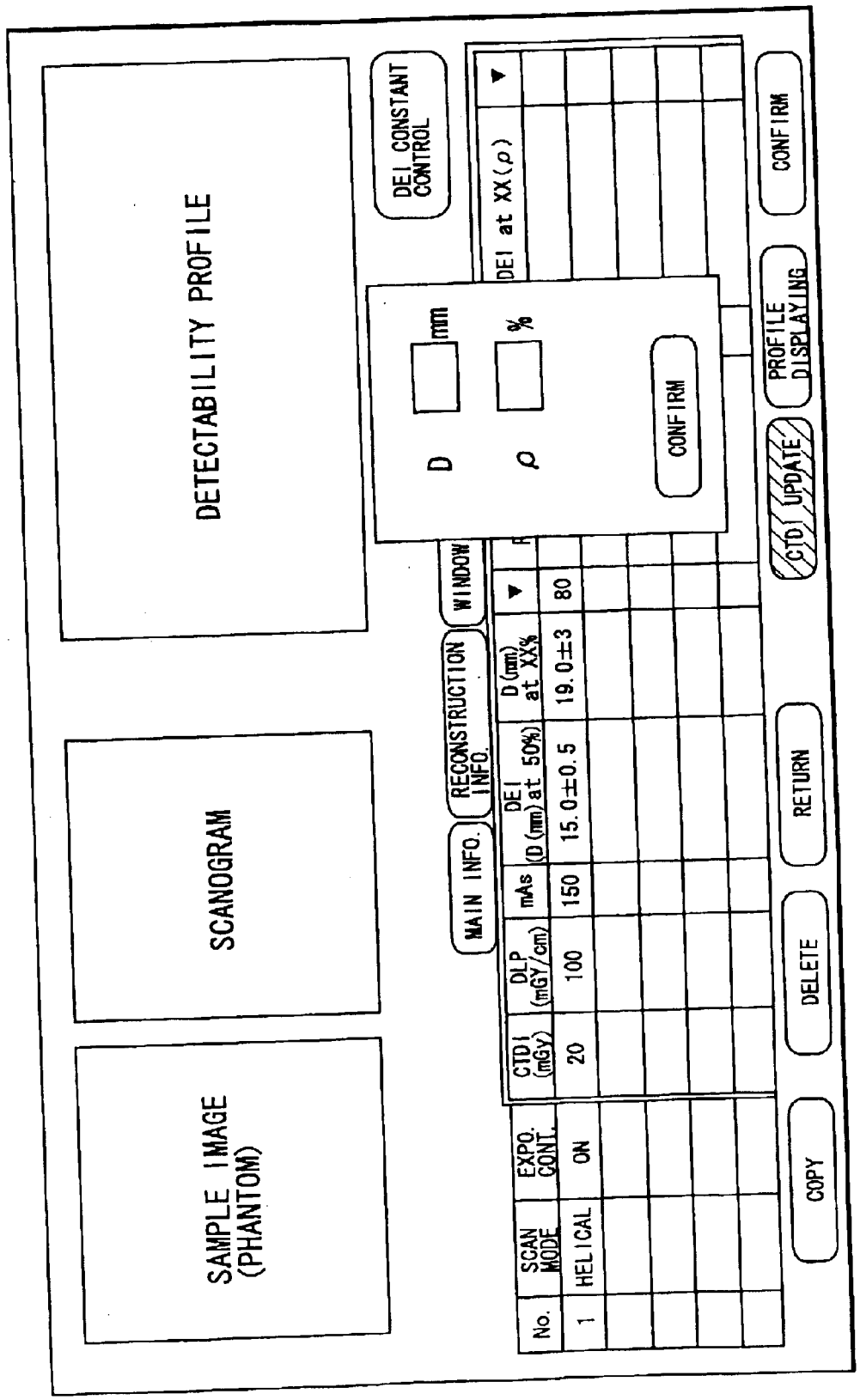
FIG. 16 is an illustration for showing another X-ray conditions setting screen built up by the plan support system of FIG. 1, especially showing an update conditions setting window which is popped up when a "CTDI" button is clicked.

For example, as shown in FIG. 15, when the "CTDI UPDATE" button is clicked, in response thereto, a sub-window pops up for setting of CTDI update conditions. This sub-window has therein a target diameter entry box, a CT value difference entry box, and a detectability rate entry box. The operator enters respective desired values into these boxes. It is to be Noted that by entering "50%" into the detectability rate entry box, a DEI value can be set. An example of a sub-window for determining the CTDI update conditions is shown in FIG. 16.

A dose "CTDI" required to meet these entry conditions is calculated by the calculator 118 in accordance with the above equation, so that based on a calculated CTDI, the plan support system 117 specifies "mAs" in accordance with an existing equation.

As can be seen from the above equation, a CTDI value required to meet the entry conditions actually varies with a difference between a transmission dose and an application dose, that is, an attenuation dose of X-ray. By controlling an mAs value corresponding to an actual transmission doze (projection data) acquired during or prior to scanning, a tube current can be controlled by the exposure controller 119 to roughly meet such conditions during scanning that a set value of DEI, that is, a set value of target diameter may be recognized at a detectability rate of 50% or the set value of target diameter may be recognized at a desired detectability rate.

In helical scanning, a position of the subject at which an X-ray is applied varies continuously. To maintain an entered DEI value at a plurality of positions on the subject, the low-contrast resolution calculator 120 specifies a CTDI value corresponding to each of the plurality of positions to calculate an mAs value corresponding to each of the plurality of positions based on this specified CTDI value. The exposure controller 119 controls the high voltage generator 109 in accordance with the calculated mAs values corresponding to the plurality of positions so that a tube current of the X-ray tube may vary as the top plate moves.

To specify a CTDI value, it is necessary to acquire an X-ray attenuation dose (OR transmission dose) corresponding to each of the plurality of positions. An X-ray attenuation dose corresponding to each of the plurality of positions can be acquired from scanogram Data. The X-ray attenuation dose corresponding to each of the plurality of positions can be acquired from projection data which is acquired during helical scanning.

Figure 18:
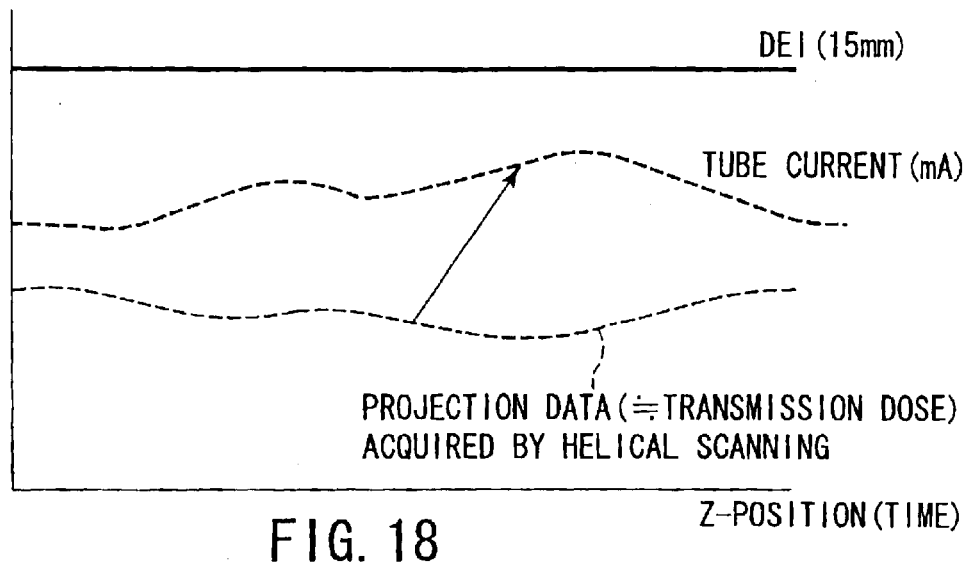
FIG. 18 is an illustration for showing a variation in Z-position of mAs due to DEI constant control of an exposure controller of FIG. 1.
Figure 19:
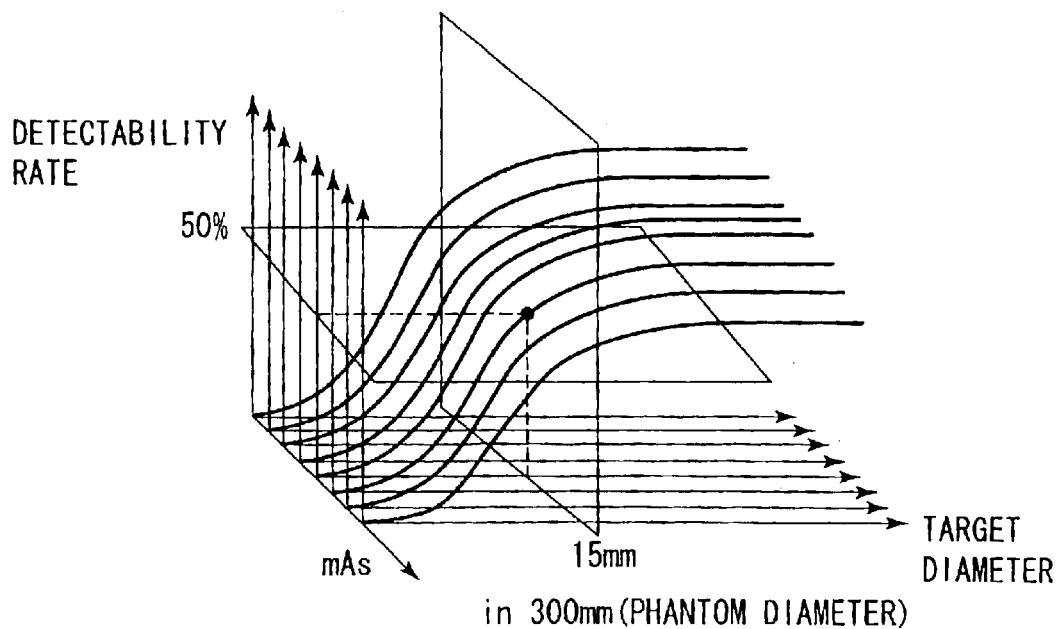
FIG. 19 is a graph for explaining an mAs determination method according to the embodiment.

FIG. 18 shows a time-wise variation controlled by the DEI constant control function in helical scanning. In this example, exposure control is shown for maintaining a DEI value at roughly 15 mm. By DEI constant control, as shown in FIG. 19, the calculator 118 determines an mAs value required to maintain the DEI at a constant value based on the immediately preceding one rotation of projection data (transmission doze) acquired in helical scanning, so that the exposure controller 119 regulates a tube current during the present scanning at a tube current during the current rotation in accordance with this decided mAs value. In this case, for example, projection data (transmission dose I) acquired during the immediately preceding one rotation at the same view angle (rotation angle α of the X-ray tube 101) and a CTDI value corresponding to DEI (=15 mm) are calculated in accordance with the above-mentioned equation (1), so that the value of mAs is set corresponding to this CTDI value. That is, the mAs value is adjusted one rotation delayed in timing corresponding to an actual transmission dose so that a set value of DEI may be maintained.

It is to be noted that the multi-channel type detector 103 uses a representative value of projection data as a transmission dose I which serves as a control factor. The representative value of projection data may be, for example, projection data acquired at a channel located at the center in a channel direction, an average value of projection data acquired at all the channels in the channel direction, an average value of projection data acquired at a predetermined number of channels located at the center in the channel direction, or even a value acquired otherwise, and is not limited in terms of method herein.

Figure 20:
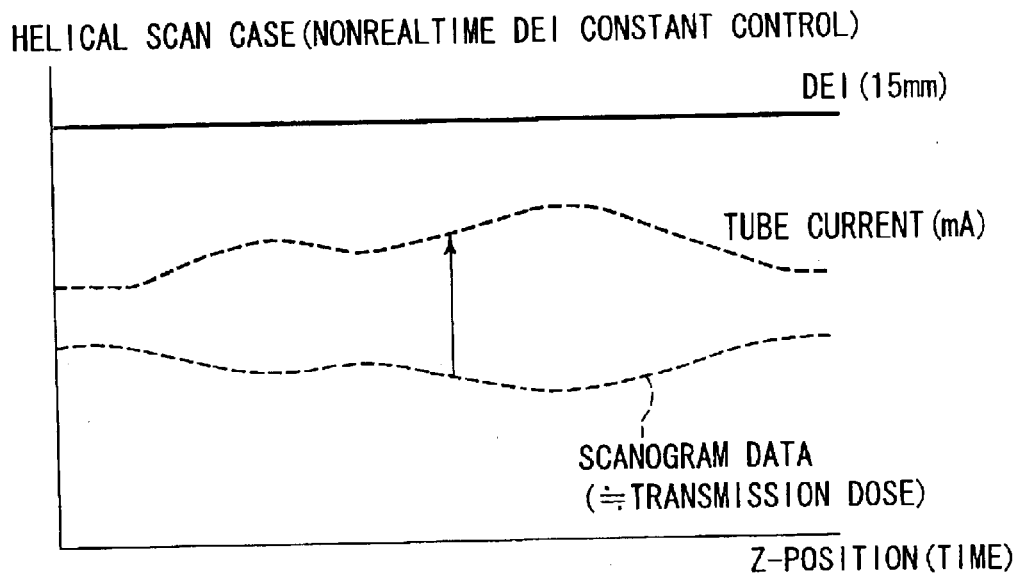
FIG. 20 is an illustration for showing a variation of mAs with respect to the Z-position due to DEI constant control of the exposure controller of FIG. 1.

In CT testing, a transmission image called a scanogram is acquired beforehand in order to determine a scanning position etc. As shown in FIG. 20, the tube current may be controlled at each imaging position (X-position) based on a transmission dose I acquired at a plurality of positions (Z-positions) from this scanogram.

Figure 21:
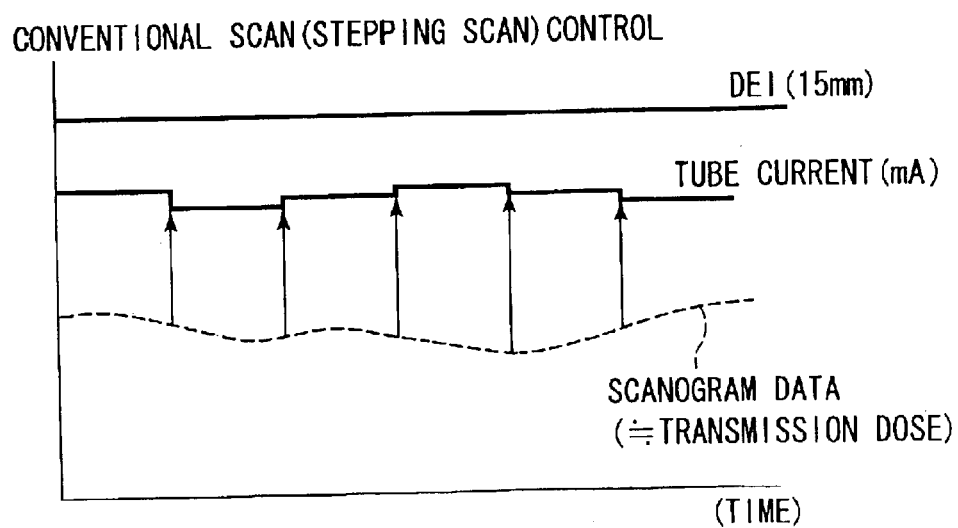
FIG. 21 is an illustration for showing a variation of mAs with respect to the Z-position due to DEI constant control of the exposure controller of FIG. 1.

Furthermore, the invention can be applied also to stepping scanning by which conventional single-slice or multi-slice scanning is repeated alternately with movement of the top plate, in which case, as shown in FIG. 21, the tube current may be controlled at each of the imaging positions (Z-positions) based on a transmission dose I acquired for each body-axial position (Z-position) from a scanogram acquired beforehand.

As described above, by the present embodiment, by deriving a relationship between a target diameter and a detectability rate that is independent of a dose, a density difference, and a transmission dose, it is possible to improve superiority of referencing a low-contrast resolution when setting scanning conditions such as a dose.

Figure 22:
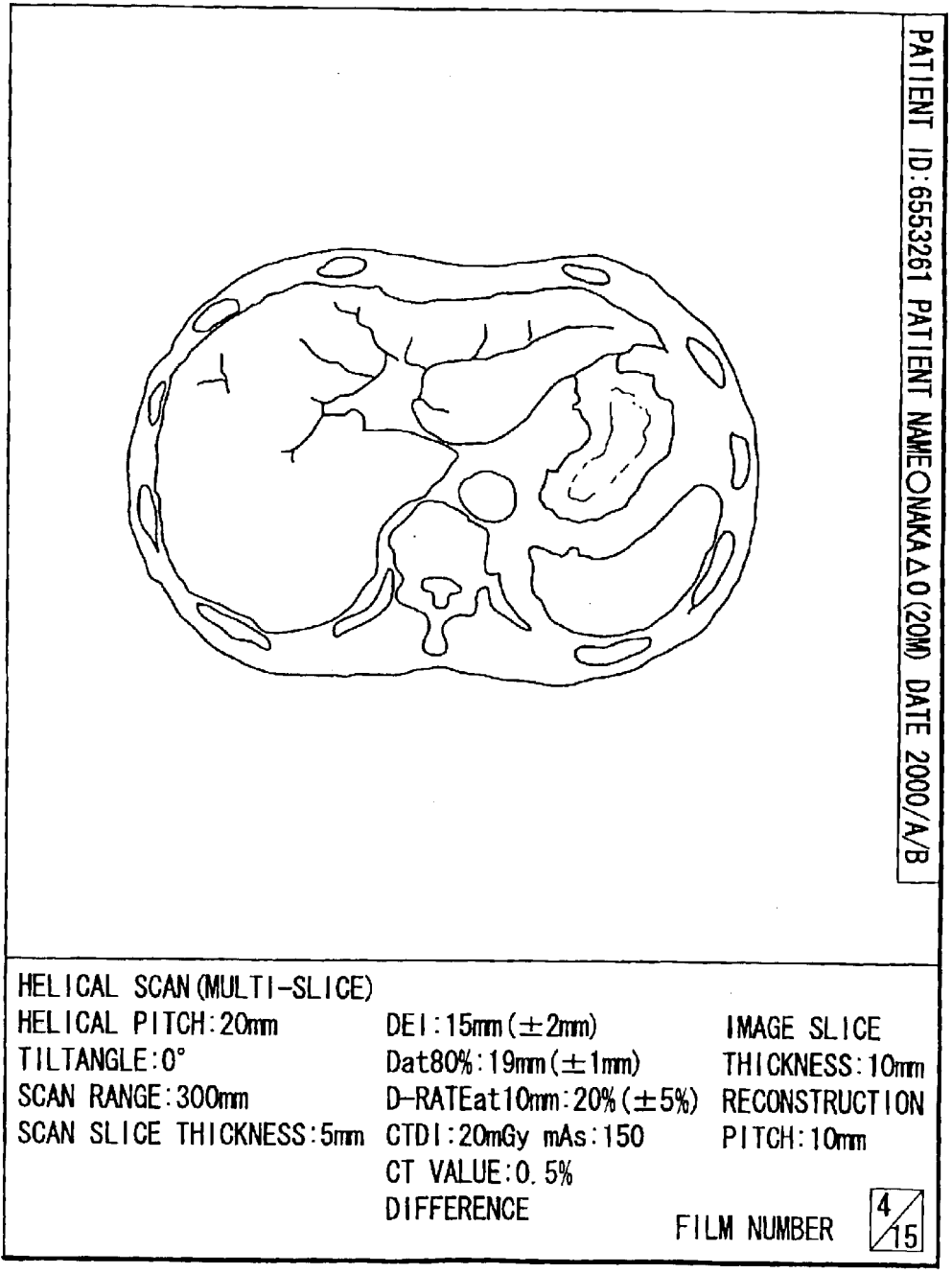
FIG. 22 is an illustration for showing a film printed by a film imager of FIG. 1.

The DEI, along with CTDI, mAs, etc., provides a very useful index in image reading. An image is read out either by viewing the image as indicated on a display or by viewing it as printed on a film. The stored data file generator 121 generates a storage data file which contains image data and data of a DEI value which is given when projection data which provides a basis of the image data is acquired. Typically, a storage data file is comprised of the header region and the data region. Image data is written into the image region. DEI data is written into the header region along with patient information etc. The print data generator 123 generates a frame data to be printed, from image data and DEI data which is given when projection data which provides a basis of the image data is acquired. An example of a film printed by the film imager 124 in accordance with the printing frame data is shown in FIG. 22.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general invention concept as defined by the appended claims and their equivalents.

What is claimed is:

1. An X-ray computed tomography apparatus which reconstructs image data based on projection data acquired by scanning a subject with an X-ray, comprising:

an input device configured to input an expected dose of the X-ray;

a calculator configured to calculate a dose efficiency index based on the expected dose, the dose efficiency index indicating a diameter of a target identified at a predetermined detectability rate and the target having a predetermined CT value difference with respect to a surrounding CT value;

a plan support system configured to build up a scan planning screen on which the input expected dose is contained along with the calculated dose efficiency index; and a display configured to display the scan planning screen.

2. The X-ray computed tomography apparatus according to claim 1, wherein the scan planning screen contains thereon a sample image which corresponds to the dose efficiency index.

3. The X-ray computed tomography apparatus according to claim 2, wherein the sample image is a phantom image.

4. The X-ray computed tomography apparatus according to claim 1, wherein the scan planning screen contains thereon a profile which represents a detectability rate as a function of a target diameter.

5. The X-ray computed tomography apparatus according to claim 1, wherein the scan planning screen contains thereon a target diameter which corresponds to an arbitrary detectability rate.

6. The X-ray computed tomography apparatus according to claim 1, wherein the scan planning screen contains thereon a detectability rate which corresponds to an arbitrary target diameter.

7. The X-ray computed tomography apparatus according to claim 1, wherein the scan planning screen contains thereon a dose efficiency index which corresponds to an arbitrary CT value difference.

8. An X-ray computed tomography apparatus which reconstructs image data based on data acquired by scanning a subject with an X-ray, comprising:

an input device configured to input a dose efficiency index, the dose efficiency index indicating a diameter of a target identified at a predetermined detectability rate and the target having a predetermined CT value difference with respect to a surrounding CT value;

a calculator configured to calculate a dose of the X-ray based on the input dose efficiency index;

a plan support system configured to build up a scan planning screen on which the input dose efficiency index is contained along with the calculated expected dose; and a display configured to display the scan planning screen.

9. The X-ray computed tomography apparatus according to claim 8, wherein the scan planning screen contains thereon a sample image which corresponds to the dose efficiency index.

10. The X-ray computed tomography apparatus according to claim 9, wherein the sample image is a phantom image.

11. The X-ray computed tomography apparatus according to claim 8, wherein the scan planning screen contains thereon a profile which represents a detectability rate as a function of a target diameter.

12. The X-ray computed tomography apparatus according to claim 8, wherein the scan planning screen contains thereon a target diameter which corresponds to an arbitrary detectability rate.

13. The X-ray computed tomography apparatus according to claim 8, wherein the scan planning screen contains thereon a detectability rate which corresponds to an arbitrary target diameter.

14. The X-ray computed tomography apparatus according to claim 8, wherein the scan planning screen contains thereon a dose efficiency index which corresponds to an arbitrary CT value difference.

15. An X-ray computed tomography apparatus which reconstructs image data based on data acquired by scanning a subject with an X-ray, comprising:

an input device configured to input an arbitrary detectability rate and a diameter of a target identified with the detectability rate;

a calculator configured to calculate a dose of the X-ray based on the input detectability rate and the input target diameter;

a plan support system configured to build up a scan planning screen on which the input detectability rate and the input target diameter are contained along with the calculated dose; and a display configured to display the scan planning screen.

16. An X-ray computed tomography apparatus which reconstructs image data based on data acquired by scanning a subject with an X-ray, comprising:

an input device configured to input a dose of the X-ray and an arbitrary dose efficiency index, the dose efficiency index indicating a diameter of a target identified at a predetermined detectability rate;

a calculator configured to calculate a CT value difference with respect to a surrounding CT value of the target so that the input dose efficiency index may be realized by the input dose of the X-ray;

a plan support system configured to build up a scan planning screen on which the input expected dose of the X-ray and the input dose efficiency index ate contained along with the calculated CT value or a value derived therefrom; and a display configured to display the scan planning screen.

17. An X-ray computed tomography apparatus which reconstructs image data based on projection data acquired by helically scanning a subject with an X-ray sent from an X-ray tube, comprising:

an input device configured to input a dose efficiency index, the dose efficiency index indicating a diameter of a target identified at a predetermined detectability rate and the target having a predetermined CT value difference with respect to a surrounding CT value;

a calculator configured to calculate doses of the X-ray which corresponds to a plurality of positions so that the input dose efficiency index may be maintained at the plurality of positions; and a controller configured to dynamically alter a tube current of the X-ray tube in accordance with the doses of the X-ray calculated at the plurality of positions.

18. The X-ray computed tomography apparatus according to claim 17, wherein the calculator calculates the doses of the X-ray based on X-ray attenuation doses which corresponds to the plurality of positions.

19. The X-ray computed tomography apparatus according to claim 17, wherein the X-ray attenuation doses are generated based on scanogram data.

20. The X-ray computed tomography apparatus according to claim 17, wherein the X-ray attenuation doses are generated based on projection data acquired by the helical scanning.

21. An X-ray computed tomography apparatus which reconstructs image data based on projection data acquired by scanning a subject with an X-ray, comprising:

a calculator configured to calculate a dose efficiency index based on a does of the X-ray, the dose efficiency index indicating a diameter of a target identified at a predetermined detectability rate and the target having a predetermined CT value difference with respect to a surrounding CT value; and a stored data file generator configured to generate a stored data file, the stored data file containing therein data relating to the calculated dose efficiency index along with the image data.

22. An X-ray computed tomography apparatus which reconstructs image data based on projection data acquired by scanning a subject with an X-ray, comprising:

a calculator configured to calculate a dose efficiency index based on a does of the X-ray, the dose efficiency index indicating a diameter of a target identified at a predetermined detectability rate and the target having a predetermined CT value difference with respect to a surrounding CT value; and a print data generator configured to generate print data, the print data containing therein data relating to the calculated dose efficiency index along with the image data.

23. An X-ray diagnostic apparatus comprising:

an X-ray source configured to radiate an X-ray;

an X-ray detector configured to detect an X-ray which has passed through a subject;

an image generator configured to generate an X-ray image based on an output of the X-ray detector; and a display configured to display an index which indicates a low contrast corresponding to a reference dose of the X-ray source on a examination planning screen to select X-ray radiation conditions of the X-ray source or image generation conditions of the image generator.

24. The X-ray diagnostic apparatus according to claim 23, wherein the index relates to statistics information which is given when imaging is performed a plurality of number of times using the reference dose.

25. The X-ray diagnostic apparatus according to claim 23, wherein the index is a size of a target which can be recognized by a detectability rate at which a target having a desired size can be recognized using the reference dose or a desired detectability rate in the reference dose.

26. The X-ray diagnostic apparatus according to claim 23, wherein the index is a graph which represents a variation of the detectability rate with respect to a variation in size of the target.

27. The X-ray diagnostic apparatus according to claim 23, wherein the index is normalized with a CT dose index (CTDI).

28. An X-ray computed tomography apparatus which reconstructs image data based on data acquired by scanning a subject with an X-ray, comprising:

a calculator configured to calculate an arbitrary one parameter of four parameters of a dose of the X-ray, a detectability rate, a diameter of a target identified at the detectability rate, and a CT value difference of the target with respect to a surrounding CT value based on the other three parameters;

a plan support system configured to build up a scan planning screen on which the three parameters are contained along with the calculated arbitrary one parameter; and a display configured to display the scan planning screen.

29. An X-ray computed tomography apparatus which reconstructs image data based on data acquired by scanning a subject with an X-ray, comprising:

an input device configured to input a CT value difference of a target with respect to a surrounding CT value;

a calculator configured to calculate a dose of the X-ray based on the input CT value difference, an arbitrary or predetermined detectability rate, and a diameter of a target identified at the detectability rate;

a plan support system configured to build up a scan planning screen on which the input CT value difference is contained along with the calculated dose; and a display configured to display the scan planning screen.

30. An X-ray computed tomography apparatus which reconstructs image data based on data acquired by scanning a subject with an X-ray, comprising:

an input device configured to input an arbitrary dose efficiency index, the dose efficiency index indicating a diameter of a target identified at a predetermined detectability rate;

a calculator configured to calculate doses of the X-ray which corresponds to a plurality of positions on the subject based on an expected concentration of a contrast-medium which corresponds to a physical constitution of the subject so that the input dose efficiency index may be maintained at the plurality of positions; and a controller configured to dynamically alter a tube current of the X-ray tube in accordance with the doses of the X-ray calculated at the plurality of positions.

31. The X-ray computed tomography apparatus according to claim 1, wherein the scan planning screen contains thereon an error range of the dose efficiency index.

32. An X-ray computed tomography apparatus which reconstructs image data based on data acquired by scanning a subject with an X-rays, comprising:

an calculator configured to calculate a parameter relative to the image data; and a display configured to display an error range of the parameter to be calculated.

* * * * *